US00PP15809P2

(12) United States Plant Patent
Bradford

(10) Patent No.: US PP15,809 P2
(45) Date of Patent: Jun. 28, 2005

(54) PLUM TREE NAMED 'YUMMY®GEM'

(50) Latin Name: *Prunus salicina*
Varietal Denomination: Yummy®gem

(76) Inventor: Lowell Glen Bradford, 12439 E. Savana Rd., Le Grand, CA (US) 95333

( * ) Notice: Subject to any disclaimer, the term of this patent is extended or adjusted under 35 U.S.C. 154(b) by 108 days.

(21) Appl. No.: 10/746,895

(22) Filed: Dec. 29, 2003

(51) Int. Cl.[7] ..... A01H 5/00

(52) U.S. Cl. ..... Plt./184

(58) Field of Search ..... Plt./184

(56) References Cited

U.S. PATENT DOCUMENTS

| | | | |
|---|---|---|---|
| PP7,503 | P | 4/1991 | Bradford |
| PP13,478 | P2 | 1/2003 | Bradford |

*Primary Examiner*—Anne Marie Grunberg

(57) ABSTRACT

The present variety of plum tree is characterized by a large size, vigorous, hardy, and very productive tree. By being self-unfruitful, blooming in the early season, and having a very prolific bloom, the present variety cross pollinates very well with 'Yummy®beaut' (U.S. Plant Pat. No. 13,478). The fruit matures under the ecological conditions described during mid June, with first picking on Jun. 12, 2003. The fruit is uniformly medium to small in size, mostly purple in skin color, clingstone in type, yellow in flesh color, very firm and crisp in texture, and very good in flavor.

1 Drawing Sheet

Botanical classification: *Prunus salicina.*
Variety denomination: 'Yummy®gem'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits. The present invention relates to a new and distinct variety of plum tree, which has been denominated varietally as 'Yummy®gem'. Yummy® is a U.S. Trademark, Ser. No. 75618722, owned by Johnny Appleseed Holdings Limited, Saint Georges Road South RD2, Hastings, New Zealand. Permission to use has been granted to the applicant by contract.

During the summer of 1993 I picked fruit from several open pollinated Purple Majesty (U.S. Plant Pat. No. 7,503) plum trees that were located in my experimental orchard located near Le Grand, Calif. in Merced County (San Joaquin Valley). The seeds from this fruit were removed, cracked, stratified and germinated as a group with the label "7P865 (OP)". They were grown as seedlings on their own root in my greenhouse and, upon reaching dormancy, transplanted to a cultivated area of the experimental orchard described above. During the summer of 1997, the present variety was selected as a single plant from the group of seedlings described above. Subsequent to origination of the present variety of plum tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is most similar to its seed parent, 'Purple Majesty' (U.S. Plant Pat. No. 7,503), by being self-unfruitful and by producing plums that are mostly purple in skin color, firm in texture, and sweet in flavor, but is distinguished therefrom by blooming about one week earlier, by being a very good pollinator for 'Yummy®beaut' (U.S. Plant Pat. No. 13,478), and by producing plums that are somewhat smaller in size but mature about twelve days earlier.

SUMMARY OF VARIETY

The present variety of plum tree is characterized by a large size, vigorous, hardy, and very productive tree. By being self-unfruitful, blooming in the early season, and having a very prolific bloom, the present variety cross pollinates very well with 'Yummy®beaut' (U.S. Plant Pat. No. 13,478). The fruit matures under the ecological conditions described during mid June, with first picking on Jun. 12, 2003. The fruit is uniformly medium to small in size, mostly purple in skin color, clingstone in type, yellow in flesh color, very firm and crisp in texture, and very good in flavor. The variety was developed from an open pollinated seed of Purple Majesty (U.S. Plant Pat. No. 7,503).

DRAWING

The accompanying photograph exhibits four whole fruits positioned to display the characteristics of the skin color and form, one fruit divided transversely to the suture plane to reveal the flesh and stone, and typical leaves.

DETAILED BOTANICAL DESCRIPTION

Referring now more specifically to the pomological characteristics of this new and distinct variety of plum tree, the following has been observed under the ecological conditions prevailing near Le Grand, Merced County (San Joaquin Valley), Calif., and was developed at the state of firm ripe on Jun. 15, 2003, on the original tree during its tenth growing season. All major color code designations are by reference to the Inter-Society Color Council, National Bureau of Standards. Common color names are also used occasionally.

TREE

Size: Large, reaching and maintaining a height of 10' [3.0 m.] and a spread of 10' [3.0 m.] after ten growing seasons utilizing typical dormant pruning.

Vigor: Vigorous, responding typically to irrigation and fertilization. The variety grows about 6' [1.8 m.] of surplus top-growth during the spring and summer. The plant should be grown on a standard commercial rootstock for production purposes.

Growth: Dense and spreading.

Form: Vase formed.

Hardiness: Hardy with respect to central California winters.

Heat tolerance: Observed to perform adequately in typical central California climatic conditions, which typically include prolonged periods of heat.

Drought tolerance: Variety is developed for commercial orchards and requires regular irrigation.

Production: Very productive, thinning usually necessary.

Fertility: Self-unfruitful, requiring cross pollination by a suitable early blooming plum, such as 'Yummy®beaut' (U.S. Plant Pat. No. 13,478).

Bearing: Regular bearer.

Trunk:

*Size.*—Stocky, reaching a maximum diameter of 8" [203 mm.] after the tenth growing season.

*Texture.*—Shaggy.

*Bark color.*—Tri-colored with Grayish yellowish brown [80. gy.yBr] over Grayish reddish brown [46. gy.rBr] with Light yellowish brown [76. l.yBr] crevices.

*Lenticels.*—Approximate Number Per Square Inch: 10. Color: Brownish orange [54. brO]. Typical Size: ⅛" to ⅜" [3.2–9.5 mm.].

Branches:

*Size.*—Limb diameter is 3½" [89 mm.] measured 12" above the secondary fork, typical of *Prunus salicina,* and dependent upon cultural practices and climatic conditions.

*Texture.*—Smooth on first year wood, increasing roughness with age.

*Color.*—1st Year Wood Topside: Moderate reddish brown [43. m.rBr]. 1st Year Wood Underside: Strong yellow green [117. s.YG]. Older Wood: 2nd year and older wood is a two-tone Dark reddish brown [44. d.rBr] with Light yellowish brown [76. l.yBr] streaking.

*Lenticels.*—Number Per Square Inch: About 100. Color: Light orange [52. l.O]. Average size: 1/32" [0.8 mm.].

Leaves:

*Size.*—Medium. Average Length: 4¼" [108 mm.]. Average width: 2¼" [57 mm.].

*Arrangement.*—Alternate.

*Thickness.*—Medium.

*Form.*—Elliptical.

*Apex.*—Acuminate.

*Base.*—Mostly rounded, some acute.

*Surface.*—Smooth.

*Color.*—Dorsal Surface: Dark olive green [126. d.OlG]. Ventral Surface: Moderate olive green [125. m.OlG].

*Margin.*—Finely serrate.

*Venation.*—Pinnately net veined.

*Petiole.*—Average Length: 7/16" [11.1 mm.]. Average Thickness: 1/16" [1.6 mm.]. Color: Light yellow green [119. l.YG] with Moderate reddish brown [43. m.rBr] tinting if exposed to sunlight.

*Stipules.*—Number: Usually 2 per leaf, up to 6 per growing tip. Average Length: ¼" [6.4 mm.]. Color: Light yellow green [119. l.YG] becoming Moderate reddish brown [43. m.rBr] with age.

*Glands.*—Number: 2 to 6 per leaf. Position: Mostly on the petiole, majority are opposite with a few somewhat alternate. Size: Small. Form: Globose. Color: Light yellow green [119. l.YG] with the centers becoming Grayish red [19. gy.R] with age.

*Leaf buds.*—Conic.

Flower buds:

*Hardiness.*—Hardy, with respect to central California winters.

*Diameter.*—Typically 3/16" [4.8 mm.] 1 week before bloom.

*Length.*—Typically ⅜" [9.5 mm.] 1 week before bloom.

*Form.*—Not appressed.

*Surface.*—Pubescent.

*Color.*—White [263. White].

Flowers: Perfect, complete, perigynous, usually a single pistil, typically thirty or more stamens, five sepals and petal locations alternately positioned.

*Average flower diameter.*—⅞" [22.2 mm.].

*Number of petals.*—Usually five.

*Petal shape.*—Somewhat oval to elliptical.

*Petal margin.*—Slightly wavy.

*Average petal diameter.*—⅜" [9.5 mm.].

*Average petal length.*—7/16" [11.1 mm.].

*Petal apex.*—Rounded.

*Petal base.*—Rounded.

*Petal color.*—White [263. White].

*Anther color.*—Brilliant orange yellow [67. brill.OY] on the edges with a Brilliant yellow [83. brill.Y] center.

*Stigma color.*—Brilliant greenish yellow [98. brill.gY].

*Sepal color.*—Light yellow green [119. l.YG] with a very thin Grayish red [19. gy.R] edge on some.

*Sepal length.*—5/32" [4.0 mm.].

*Sepal width.*—⅛" [3.2 mm.].

*Average pistil length.*—7/16" [11.1 mm.].

*Average stamen length.*—⅜" [9.5 mm.].

*Fragrance.*—Moderate.

*Pollen production.*—Very Abundant.

*Blooming period.*—Early compared with other varieties, with 'Ambra' (unpatented).

*Onset of bloom.*—One percent on Feb. 14, 2003.

*Date of full bloom.*—Feb. 26, 2003.

*Duration of bloom.*—One to two weeks, dependent on ambient temperature.

*Number per cluster.*—2 to 7, average 4.

FRUIT

Maturity when described: Firm ripe, Jun. 15, 2003.

Date of first picking: Jun. 12, 2003.

Date of last picking: Jun. 21, 2003.

Size: Uniform, small to medium.

*Average diameter axially.*—2" [50.8 mm.].

*Average diameter across suture plane.*—2¼" [57.2 mm.].

*Typical weight.*—3.8 ounces [108 grams].

Form: Uniform, symmetrical.

*Longitudinal section form.*—Oval to somewhat obovate.

*Transverse section through diameter.*—Round.

Suture: An inconspicuous Blackish red [21. blackish R] line located in a shallow groove extending from the base and discontinuing at the apex with a slight depression at pistil point.
Ventral surface: Rounded.
Lips: Virtually none.
Cavity: Flaring, circular to slightly elongated in suture plane, suture showing on one side.
*Depth.*—5/16" [7.9 mm.].
*Breadth.*—7/8" [22.2 mm.].
Base: Truncate.
Apex: Rounded.
Pistil point: An negligible Light yellowish brown [76. l.yBr] dot.
Stem: Medium.
*Average length.*—5/16" [7.9 mm.].
*Average width.*—1/16" [1.6 mm.].
Skin:
*Thickness.*—Medium.
*Surface.*—Smooth.
*Tenacity.*—Tenacious to flesh.
*Astringency.*—Somewhat astringent.
*Tendency to crack.*—Very slight in wet season.
*Color.*—Very deep purplish red [257. v.deep pR] over a Very deep red [14. v.deep R] background with Light yellowish brown [76. l.yBr] freckling throughout, except along the suture.
*Bloom.*—Abundant.
Flesh:
*Color.*—Light greenish yellow [101. l.gY] toward the stone smoothly blending to Strong yellow [84. s.Y] toward the skin.
*Surface of pit cavity.*—Light greenish yellow [101. l.gY] to Moderate yellow [87. m.Y] broken fibers when twisted away from the stone.
*Amygdalin.*—Moderate.
*Juice.*—Abundant, rich.
*Texture.*—Firm, crisp.
*Fibers.*—Abundant, fine, tender.
*Ripens.*—Slightly earlier at the apex and along the suture.
*Flavor.*—Tasty blend of acid and sugar, typically 16 to 18 brix.
*Aroma.*—Slight.
*Eating quality.*—Very good.

STONE

Type: Clingstone.
Form: Oval to circular.
Hilum: Narrow.
Base: Straight.
Apex: Cuneate with an average angle of 110 degrees and a very sharp tip.
Sides: Equal.
Surface: Rough.
External color of stone: Light yellowish brown [76. l.yBr] when first exposed.
Pit wall color when cracked: Light yellowish brown [76. l.yBr].
Cavity surface color: Pale orange yellow [73. p.OY].
Average pit wall thickness: 1/16" [1.6 mm.].
Average width: 15/16" [23.8 mm.].
Average length: 1" [25.4 mm.].
Average breadth: 7/16" [11.1 mm.].
Tendency to split: Slight when girdled.
Kernel:
*Form.*—Oval.
*Skin color.*—Light yellow [86. l.Y] when first cracked turning Brownish orange [54. brO] when dry.
*Pellicle color.*—Light grayish yellowish brown [79. l.gy.yBr].
*Vein color.*—Light grayish yellowish brown [79. l.gy.yBr].
*Taste.*—Bitter.
*Viable.*—Yes.
*Average width.*—7/16" [11.1 mm.].
*Average length.*—9/16" [14.3 mm.].
*Amygdalin.*—Abundant.

USE

Market: Fresh market and long distance shipping.
Keeping quality: Excellent. Fruit quality observed to remain in good condition in after 30 days in standard cold room at 36° Fahrenheit [2° Celsius].
Shipping quality: Excellent.
Resistance to insects: No unusual susceptibilities noted.
Resistance to diseases: No unusual susceptibilities noted.

Other Notes

Although the new variety of plum tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of plum tree, substantially as illustrated and described, that is most similar to its seed parent, 'Purple Majesty' (U.S. Plant Pat. No. 7,503), by being self-unfruitful and by producing plums that are mostly purple in skin color, firm in texture, and sweet in flavor, but is distinguished therefrom by blooming about one week earlier, by being a very good pollinator for 'Yummy®beaut' (U.S. Plant Pat. No. 13,478), and by producing plums that are somewhat smaller in size but mature about twelve days earlier.

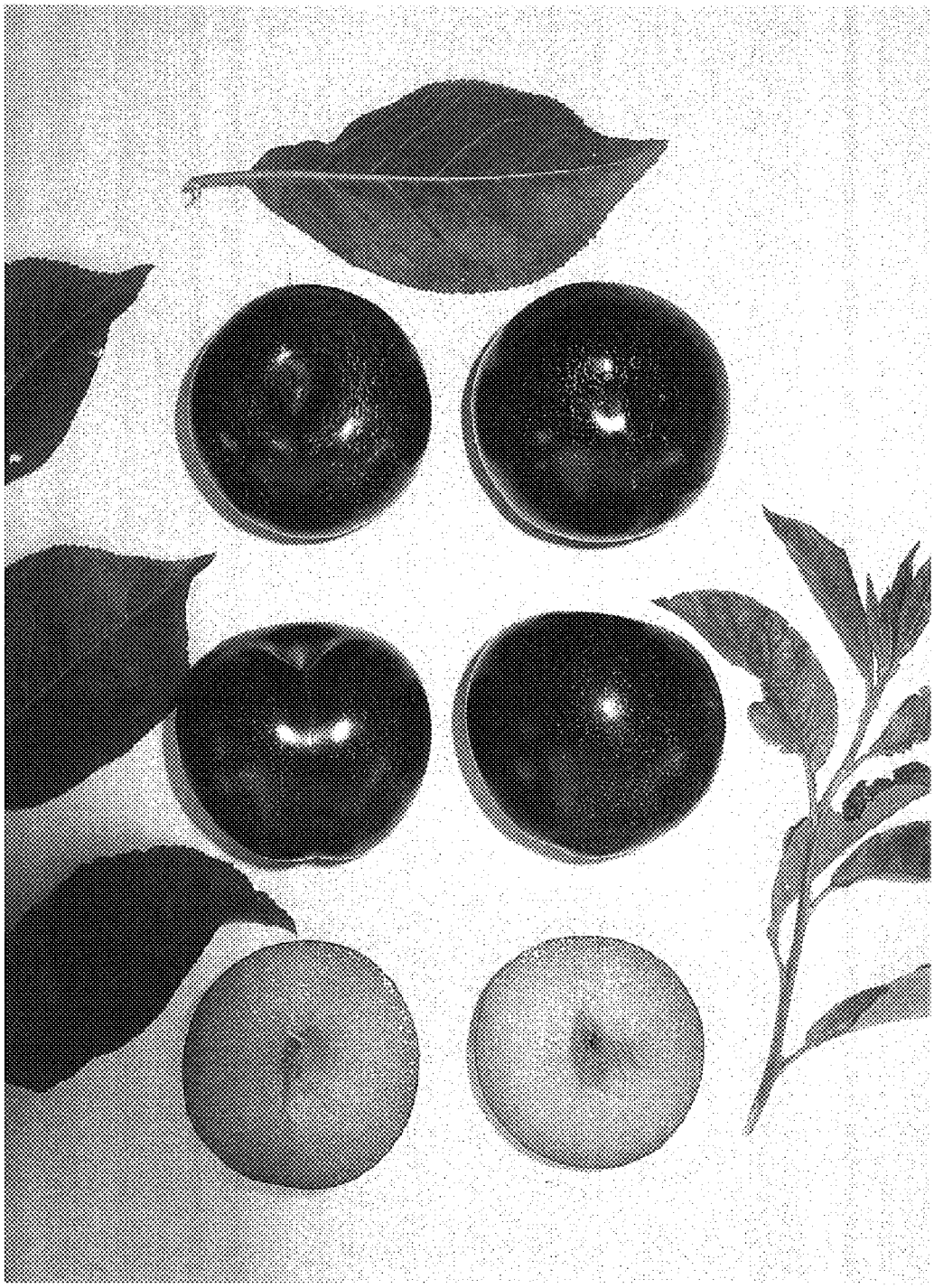

* * * * *